United States Patent [19]

Bruchmann et al.

[11] Patent Number: 5,637,664
[45] Date of Patent: Jun. 10, 1997

[54] POLYMERIC, CATALYTICALLY ACTIVE COMPOUNDS, THEIR PREPARATION, AND THEIR USE AS CATALYSTS IN THE PREPARATION OF POLYISOCYANATES CONTAINING URETDIONE GROUPS

[75] Inventors: Bernd Bruchmann, Ludwigshafen; Roland Minges, Gruenstadt; Christian Schade, Ludwigshafen; Konrad Stiefenhoefer, Ebertsheim, all of Germany

[73] Assignee: BASF Aktiengesellschaft, Ludwigshafen, Germany

[21] Appl. No.: 456,440

[22] Filed: Jun. 1, 1995

Related U.S. Application Data

[62] Division of Ser. No. 58,888, May 10, 1993, Pat. No. 5,449,775.

[30] Foreign Application Priority Data

Jun. 5, 1992 [DE] Germany .......................... 42 18 539.4

[51] Int. Cl.⁶ .......................... C08G 18/02; C08G 18/62
[52] U.S. Cl. .......................... 528/73; 521/137; 525/416; 528/125; 528/303; 528/371
[58] Field of Search .......................... 525/281, 416, 525/450, 455, 471; 521/137; 528/73, 125, 303, 371

[56] References Cited

U.S. PATENT DOCUMENTS

| | | | |
|---|---|---|---|
| 3,290,288 | 12/1966 | Oertel et al. | 540/202 |
| 3,919,195 | 11/1975 | Bakhitov et al. | 540/202 |
| 4,336,365 | 6/1982 | Reischl et al. | 528/44 |
| 4,595,534 | 6/1986 | Scholl | 540/202 |
| 4,687,813 | 8/1987 | Lenz et al. | 525/131 |
| 4,786,655 | 11/1988 | Grögler et al. | 528/45 |
| 4,797,455 | 1/1989 | Lin et al. | 525/504 |
| 4,894,429 | 1/1990 | Grogler et al. | 528/45 |
| 4,912,210 | 3/1990 | Disteldorf et al. | 540/202 |
| 4,929,724 | 5/1990 | Engbert et al. | 521/93 |
| 4,996,281 | 2/1991 | So | 528/73 |
| 5,106,875 | 4/1992 | Horn et al. | 521/137 |
| 5,149,766 | 9/1992 | Bruchmann | 528/49 |
| 5,315,004 | 5/1994 | Goldstein et al. | 540/202 |

FOREIGN PATENT DOCUMENTS

| | | |
|---|---|---|
| 317744 | 5/1989 | European Pat. Off. . |
| 368217 | 5/1990 | European Pat. Off. . |
| 418639 | 3/1991 | European Pat. Off. . |
| 417603A2 | 3/1991 | European Pat. Off. . |
| 431331 | 6/1991 | European Pat. Off. . |
| 46-37503 | 2/1968 | Japan . |
| 0100148 | 8/1976 | Poland . |
| 821158 | 9/1959 | United Kingdom . |

OTHER PUBLICATIONS

Synthesis, 463–464, 1975.
Recent Advances in Isocyanate Chemistry, Chemical Review, 47–73, 1957.
Chemical Abstracts Registry, 1994.
Dictionary of Organic Compounds, vol. 3, 5th Ed., pp. 3287–3288, 1982.
Chemsources—USA, 1994 Edition.

*Primary Examiner*—Yogendra N. Gupta
*Attorney, Agent, or Firm*—Fernando A. Borrego

[57] ABSTRACT

Polymeric, catalytically-active compounds having imidazole groups linked terminally and/or laterally to the polymer chain through reactive groups on the polymer chain are disclosed. The polymer chain is selected from the group consisting of polyether ketones; acidic, basic, or neutral ion exchange resins; polymeric isocyanates; polymers or copolymers containing maleic acid or maleic anhydride; and polymers containing benzyl halide groups.

8 Claims, No Drawings

POLYMERIC, CATALYTICALLY ACTIVE COMPOUNDS, THEIR PREPARATION, AND THEIR USE AS CATALYSTS IN THE PREPARATION OF POLYISOCYANATES CONTAINING URETDIONE GROUPS

This is a division, of application Ser. No. 08/058,888, filed May 10, 1993, now U.S. Pat. No. 5,449,775.

The present invention relates to polymeric, catalytically active compounds which are suitable as catalysts in the preparation of polyisocyanates containing uretdione groups, and to their preparation and use.

It is known that uretdiones can be prepared by converting isocyanates in the presence of catalysts. Suitable catalysts are various substances, eg. trialkylphosphines, as described in DE-A 30 05 106, trialkyl phosphites, as described in DE-A 23 49 726, triaminophosphines, as described in U.S. Pat. No. 3,290,288 and DE-A 34 37 635, cycloamidines, as described in JP-A 46/37 503, pyridine or substituted pyridines, as described in GB-A 821,158, and organometallic compounds, eg. bismuth or antimony compounds, as described in DE-A 36 40 855 and DE-A 34 20 114.

The imidazoles and benzimidazoles as described in EP-A-0 417 603 have proven particularly suitable. They give high yields and high selectivity, in particular with respect to suppression of the formation of isocyanurates.

It is common to these known catalysts that the catalyst must be removed from the reaction mixture or deactivated by suitable measures after the dimerization. If the catalyst remains in the product, it may, by catalyzing undesired side reactions, interfere with the reactions in which the dimer is employed as starting material. In addition, it is possible for the catalyst to migrate on thermal treatment of the isocyanates or the products prepared therefrom, which must be avoided due to the health risk posed by many of the catalysts.

The catalyst is usually removed during washing or recrystallization of the dimer. Since the product cannot be heated, removal of the catalyst by distillation is not possible. Washing of the uretdione requires considerable amounts of solvent. The catalyst must either be recovered from the large amounts of solvent or deactivated by suitable chemicals.

In the known methods, recovery of the catalyst without significant losses is difficult. After deactivation, considerable amounts of the deactivated compound frequently remain in the product.

It is an object of the present invention to find compounds which are suitable as catalysts for the formation of uretdiones, can easily be removed after reaction and can be reused after suitable work-up.

We have found that, surprisingly, this object is achieved by carrying out the process for the preparation of polyisocyanates containing uretdione groups using, as catalysts, polymeric, catalytically active compounds in which imidazole groups are attached terminally and/or laterally to the polymer chains via reactive groups.

The present invention accordingly provides polymeric, catalytically active compounds wherein imidazole groups are linked terminally and/or laterally to the polymer chains via reactive groups. The imidazole groups may be substituted or unsubstituted.

The imidazole groups have, in particular, the formula (I) or (II)

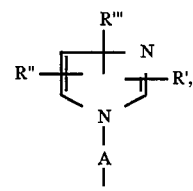

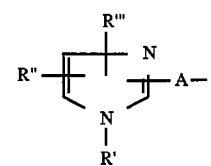

where

R', R" and R'" are identical or different and are hydrogen, $C_1$- to $C_2$-alkyl, aryl, aralkyl, alkylaryl, $C_1$- to $C_{12}$-heteroalkyl, heteroaryl, $C_1$- to $C_{12}$-alkenyl, $C_1$- to $C_{12}$-alkynyl, hydroxyl, mercapto, amino, isocyanate, halogen, sulfonyl or sulfynyl;

A is a single chemical bond, $C_1$- to $C_{12}$-alkylene, arylene, $C_1$- to $C_{12}$-heteroalkylene, heteroarylene, $C_2$- to $C_{12}$-alkenylene, $C_2$- to $C_{12}$-alkynylene, sulfonyl or sulfynyl, the amidazole group being linked to the polymer chain via A.

The linking is achieved by reacting reactive groups connected to the imidazole via A with reactive groups which are capable of reacting with the former reactive groups and are attached terminally and/or laterally to the polymer chain.

The reactive groups may be, for example, carboxyl, carboxylic anhydride, hydroxyl, amino, isocyanate, mercapto, aldehyde, keto, epoxy, halogen or chloroformate groups.

The polymer chains, which may be crosslinked or uncrosslinked, may be conventional polymers carrying reactive groups, such as polyether ketones, acidic, basic or neutral ion exchanger resins, polymeric isocyanates, polymers and copolymers containing maleic acid or maleic anhydride, or polymers containing benzyl halide groups, known as Merrifield resins.

The imidazoles employed are at least monofunctionalized imidazoles.

The reaction of the imidazoles with the polymers is carried out under reaction conditions under which the reactive groups on the polymer chain and on the functionalized imidazoles usually react with one another. The polymeric compounds containing imidazole groups are then worked up by methods which are known in general terms.

The polymeric compounds obtained in this way can, in order to improve their mechanical properties, such as solvent resistance, abrasion resistance or processing properties, be mixed with conventional polymers, such as polyethylene, polypropylene, polyvinyl chloride, polytetrafluoroethylene or polymethyl methacrylate. These blends can be prepared by methods which are conventional for this purpose, for example by extrusion with subsequent granulation.

The novel polymers containing imidazole groups can be employed, for example, as urethane formation catalysts, as ion exchangers, but preferably as catalysts for the dimerization of isocyanates.

The dimerization of isocyanates in the presence of the catalytically active compounds according to the invention is carried out in the presence or absence of an aprotic solvent. The reaction temperature is from −20° to 150° C., preferably from 0° to 80° C., and the concentration of the catalytically active compound is at least 0.001% by weight, based on the isocyanate.

The isocyanates employed can be aromatic isocyanates, eg. phenyl isocyanate, tolyl isocyanate, 1,5-naphthalene diisocyanate, 1,4-phenylene diisocyanate, 2,4-tolylene diisocyanate (2,4-TDI), 2,6-tolylene diisocyanate (2,6-TDI), 4,4'-diphenylmethane diisocyanate (4,4'-MDI), 2,4'-diphenylmethane diisocyanate (2,4'-MDI) or mixtures thereof.

The solvents employed are aprotic solvents, such as benzene, toluene, chlorobenzene, ketones, such as acetone or methyl ethyl ketone, alkanes or halogenated alkanes, such as methylene chloride, chloroform, tetrachloromethane or n-, iso- or cycloalkanes.

The dimerization reaction usually commences rapidly after the catalyst has been added. When the desired conversion has been reached, the polymeric catalyst according to the invention can be removed from the reaction mixture very simply, for example by filtration. The uretdione can then be crystallized by cooling and separated off, for example by filtration. The separated-off uretdione is washed with an aprotic solvent and then dried, usually under reduced pressure in order to avoid thermal decomposition.

The recovered catalyst can be reused, without treatment, for a further dimerization batch.

It is also possible to carry out the dimerization continuously by passing the isocyanate, if desired in solution, over the polymeric catalyst in the form of a fixed bed.

If the catalytic activity of the catalyst drops due to contamination with isocyanate reaction products, it can be freed from adherent products by heating or by treatment with a solvent and thus reactivated.

EXAMPLES

EXAMPLE 1

Preparation of the polymeric catalysts A to E 30 g of a copolymer of diisobutene (DIB) and maleic anhydride (MAA) in a molar ratio of 1:1 were dissolved in 200 ml of toluene at 100° C. in a reactor fitted with water separator. The imidazole and, if desired, a crosslinking agent were then dissolved in 50 ml of toluene and added dropwise over the course of 30 minutes.

The mixture was heated at the boil until water of reaction no longer accumulated in the water separator, and was then cooled, and the resultant precipitate was filtered off with suction, washed with hot toluene and dried at 60° C. under reduced pressure.

Tables 1 and 2 show 7 catalyst batches. Imidazoles used:
1-(3-aminopropyl)imidazole (1)
1-(3-aminopropyl)-2-methylimidazole (2)
1-(3-aminopropyl)-2-ethyl-4-methylimidazole (3)
1-(2-hydroxyethyl)-2-methylimidazole (4)
2-methylimidazole (5)

TABLE 1

Polymeric catalysts, yields and melting ranges

| Catalyst | Imidazole (g) | Crosslinking agent (g) | Yield of polymer (%) | Melting range [°C.] |
|---|---|---|---|---|
| A | 1 (6.8) | HDA[+) (6.0) | 95 | from 203 |
| B | 2 (12.6) | — | 85 | 172–97 |
| C | 2 (12.6) | HDA (3.2) | 98 | from 190 |

TABLE 1-continued

Polymeric catalysts, yields and melting ranges

| Catalyst | Imidazole (g) | Crosslinking agent (g) | Yield of polymer (%) | Melting range [°C.] |
|---|---|---|---|---|
| D | 2 (7.0) | HDA (6.0) | 95 | from 205 |
| E | 3 (16.2) | — | 80 | 155–180 |
| F | 4 (90) | — | 96 | >280 |
| G | 5 (90) | — | 97 | >280 |

[+)Hexamethylenediamine

TABLE 2

Composition of the polymer catalysts according to elemental analysis, nitrogen content

| Catalyst | Nitrogen [%] Calculated | Found |
|---|---|---|
| A | 8.7 | 8.8 |
| B | 8.9 | 7.7 |
| C | 10.1 | 9.9 |
| D | 8.3 | 8.1 |
| E | 8.8 | 7.6 |
| F | 8.7 | 6.3 |
| G | 10.0 | 8.3 |

EXAMPLE 2

Preparation of catalysts F and G 30 g of Merrifield resin from Fluka containing 4.3 mmol of active chlorine/mol were heated to 150° C. with the corresponding imidazole under a blanket of nitrogen in a reactor, and the mixture was kept at this temperature for 6 hours. The reaction mixture was cooled to 20° C. and washed successively with 200 ml of acetone, 300 ml of 15% strength aqueous sodium hydroxide solution, 300 ml of distilled water and finally with 200 ml of acetone. The product was then dried at 80° C. under reduced pressure.

EXAMPLE 3

Preparation of catalyst H 150 g of catalyst D from Example 1 were mixed with 150 g of BASF Lupolen PE-HID 5261Z polyethylene, and the mixture was extruded at 250° C. and then granulated to give pellets 5 mm in length and 3 mm in diameter.

EXAMPLE 4

Dimerization of aromatic isocyanates 1000 g of isocyanate, the polymer catalyst from Example 1 and, if desired, 1000 g of solvent were warmed to 50° C. and stirred. After the reaction time shown in Table 3, the catalyst was removed by suction filtration. On cooling, the dimer crystallized as a solid. After 12 hours, it was filtered off with suction, washed with toluene or methyl ethyl ketone and dried at 60° C. under reduced pressure.

The uretdiones still contained a little adhering monomer. Isocyanurates, which cause mostly undesired crosslinking when the uretdione is used in polyurethane systems, were below the detection limit (1% by weight).

The reaction data for the dimerization are shown in Table 3.

TABLE 3

Reaction data for the dimerization, yields and melting points

| Isocyanate | Solvent | Catalyst (g) | Reaction time (h) | Yield [%] | Dimer m.p. [°C.] |
|---|---|---|---|---|---|
| 2,4-TDI | toluene | A (20) | 1 | 38 | 152–160 |
| 2,4-TDI | — | B (5) | 4 | 10 | 156 |
| 2,4-TDI | MEK | C (20) | 2 | 61 | 153–159 |
| 2,4-TDI | MEK | D (20) | 1 | 60 | 153–159 |
| 2,4-TDI | MEK | E (20) | 1.5 | 55 | 155–157 |
| 4,4'-MDI | MEK | B (20) | 1.5 | 45 | 246–268 |
| 2,4/2,6-TDI 80:20 | — | F (30) | 4 | 8 | 154–156 |
| 2,4'/4,4'-MDI 50:50 | MEK | F (20) | 4 | 10 | 200–238 |

EXAMPLE 5

1000 g of a mixture of 2,4- and 2,6-TDI in the ratio 80:20 were warmed to 80° C. in a reactor, 100 g of catalyst H from Example 4 were added, and the mixture was stirred at this temperature for 2 hours and then cooled to 20° C. The catalyst was removed at this temperature by filtration, 2000 g of methyl ethyl ketone were added to the isocyanate mixture, and the solution was left to stand at 20° C. for 16 hours.

The resultant precipitate of TDI dimers was filtered off, washed with 500 g of methyl ethyl ketone and dried at 60° C. under reduced pressure. The yield of dimers was 500 g, and the melting range was from 155° to 158° C.

EXAMPLE 6

Reusability of the catalyst 1000 g of 2,4-TDI, 50 g of catalyst C from Example 1 and 1000 g of methyl ethyl ketone were stirred at 40° C. for 1 hour. The catalyst was filtered off with suction (filtrate 1), reemployed for 1 hour at 40° C. with 1000 g of 2,4-TDI and 1000 g of methyl ethyl ketone, filtered off with suction and used a third time (filtrates 2 and 3). The catalyst was subsequently boiled with dioxane and reemployed for the dimerization. Suction filtration gave filtrate 4. The TDI dimer crystallized from the filtrates, was filtered off with suction after 12 hours and was dried as in Example 2. The following yields were achieved:

| Filtrate 1: 694 g | (69%) |
|---|---|
| Filtrate 2: 583 g | (58%) |
| Filtrate 3: 90 g | (9%) |
| Filtrate 4: 395 g | (40%) |

The dimers had melting points of 153°–159° C.

We claim:

1. A polymeric, catalytically active compound, having imidazole groups linked terminally and/or laterally to the polymer chain through reactive groups on the polymer chain, said polymer chain having said reactive groups selected from the group consisting of polyether ketones; acidic, basic, or neutral ion exchange resins; polymeric isocyanates; polymers or copolymers containing maleic acid or maleic anhydride; and polymers containing benzyl halide groups.

2. A polymeric, catalytically active compound as claimed in claim 1, wherein substituents are located on the imidazole groups.

3. A polymeric, catalytically active compound as claimed in claim 2, wherein the polymer chains are branched and/or crosslinked.

4. A polymeric, catalytically active compound as claimed in claim 3, which is blended with other polymers.

5. A polymeric, catalytically active compound as claimed in claim 1, wherein the polymer chains are branched and/or crosslinked.

6. A polymeric, catalytically active compound as claimed in claim 1, wherein the compound is blended with other polymers.

7. A polymeric, catalytically active compound as claimed in claim 2, wherein the compound is blended with other polymers.

8. A polymeric, catalytically active compound as claimed in claim 1, wherein said imidazole groups are substituted with hydrogen, $C_1$–$C_{12}$-alkyl, aryl, aralkyl, alkaryl, $C_1$–$C_{12}$-heteroaryl, $C_1$–$C_{12}$-alkenyl, and/or $C_1$–$C_{12}$-alkynyl groups.

* * * * *